(12) United States Patent
Chieng

(10) Patent No.: US 10,716,593 B2
(45) Date of Patent: Jul. 21, 2020

(54) APPARATUS FOR GUIDING A SURGICAL NEEDLE

(71) Applicant: Yen Yung Chieng, Hamilton (NZ)

(72) Inventor: Yen Yung Chieng, Hamilton (NZ)

(*) Notice: Subject to any disclaimer, the term of this patent is extended or adjusted under 35 U.S.C. 154(b) by 218 days.

(21) Appl. No.: 15/520,344

(22) PCT Filed: Oct. 20, 2015

(86) PCT No.: PCT/NZ2015/050174
§ 371 (c)(1),
(2) Date: Apr. 19, 2017

(87) PCT Pub. No.: WO2016/064282
PCT Pub. Date: Apr. 28, 2016

(65) Prior Publication Data
US 2017/0311978 A1    Nov. 2, 2017

(30) Foreign Application Priority Data

Oct. 24, 2014  (NZ) .......................... 701196

(51) Int. Cl.
*A61B 17/34*        (2006.01)
*A61B 90/11*        (2016.01)
(Continued)

(52) U.S. Cl.
CPC ...... *A61B 17/3403* (2013.01); *A61B 10/0233* (2013.01); *A61B 34/30* (2016.02);
(Continued)

(58) Field of Classification Search
CPC ... A61B 90/11; A61B 90/13; A61B 2090/067; A61B 2017/3407; A61B 90/10;
(Continued)

(56) References Cited

U.S. PATENT DOCUMENTS 4,592,352 A * 6/1986 Patil ................. A61B 90/11
                                             5/637
4,638,798 A * 1/1987 Shelden ............. A61B 6/501
                                             600/429

(Continued)

FOREIGN PATENT DOCUMENTS

EP    2567668 A1    3/2013
GB    2094590 A     9/1982
(Continued)

OTHER PUBLICATIONS

Written Opinion of the International Preliminary Examining Authority for PCT/NZ2015/050174, dated Sep. 21, 2016.
(Continued)

*Primary Examiner* — Bill Thomson
*Assistant Examiner* — Aminah Asghar
(74) *Attorney, Agent, or Firm* — Procopio, Cory, Hargreaves & Savitch LLP

(57) ABSTRACT

An apparatus (100) for guiding a surgical needle with improved accuracy. The apparatus (100) having a base (1) for positioning the apparatus (100) on a patient; a second arc member (6) attached to the base (1); a first arc member (4) moveably attached to the second arc member (6); an arm (2) attached to a needle guide support (3) at one end and moveably attached to the first arc member (4) at a distal end, and an angle marking device (7) attached to the arm (2) to indicate a vertical reference point for measuring the angle of tilt of the arm (2) from the vertical reference point relative to the base (1). Wherein the first arc member (4) is configured to move on the second arc member (6) to facilitate movement of the needle guide support (3) in a cranio-caudal plane and the arm (2) is configured to move on the first arc member (4) to facilitate movement of the needle guide support (3) in an axial plane.

8 Claims, 23 Drawing Sheets

(51) Int. Cl.
  *A61B 10/02* (2006.01)
  *A61B 34/30* (2016.01)
  *A61B 90/00* (2016.01)
  *A61B 90/13* (2016.01)
  *G01R 33/28* (2006.01)

(52) U.S. Cl.
  CPC ............... *A61B 90/11* (2016.02); *A61B 90/13* (2016.02); *A61B 2017/3407* (2013.01); *A61B 2090/067* (2016.02); *A61B 2090/069* (2016.02); *G01R 33/285* (2013.01)

(58) Field of Classification Search
  CPC ..... A61B 90/101; A61B 90/103; A61B 90/14; A61B 90/16–18
  See application file for complete search history.

(56) References Cited

U.S. PATENT DOCUMENTS

| | | | | |
|---|---|---|---|---|
| 4,841,967 A * | 6/1989 | Chang | ................ | A61B 17/3403 606/130 |
| 4,883,053 A | 11/1989 | Simon | | |
| 5,129,911 A * | 7/1992 | Siczek | ................ | A61B 6/0435 378/162 |
| 2004/0024387 A1* | 2/2004 | Payandeh | ............... | A61B 90/11 606/1 |
| 2006/0100501 A1* | 5/2006 | Berkelman | ........ | A61B 17/3403 600/415 |
| 2009/0234369 A1* | 9/2009 | Bax | .................... | A61B 17/3403 606/130 |
| 2011/0118541 A1* | 5/2011 | Gassmann | ............. | A61B 90/11 600/102 |
| 2013/0066192 A1* | 3/2013 | Sarvestani | ......... | A61B 17/3403 600/424 |
| 2013/0066232 A1* | 3/2013 | Schoepp | ............ | A61B 17/3403 600/567 |
| 2013/0066334 A1* | 3/2013 | Schoepp | ............ | A61B 17/3403 606/130 |
| 2014/0005522 A1* | 1/2014 | Zurovcik | ........... | A61B 10/0233 600/411 |
| 2014/0275979 A1 | 9/2014 | Fujimoto et al. | | |
| 2014/0336670 A1* | 11/2014 | Brabrand | .............. | A61B 90/11 606/130 |

FOREIGN PATENT DOCUMENTS

| | | |
|---|---|---|
| WO | 2008/047379 A2 | 4/2008 |
| WO | 2009/015548 A1 | 2/2009 |
| WO | 2010/084322 A1 | 7/2010 |

OTHER PUBLICATIONS

International Preliminary Report on Patentability for PCT/NZ2015/050174, dated Dec. 19, 2016.
International Search Report and Written Opinion for PCT/NZ2015/050174, dated Nov. 24, 2015.
Examination Report dated Jan. 23, 2020 for related EP Patent Application No. 15851801.9, in 5 pages.

* cited by examiner

APPARATUS FOR GUIDING A SURGICAL NEEDLE

STATEMENT OF CORRESPONDING APPLICATIONS

This application is based on the Provisional specification filed in relation to New Zealand Patent Application Number 701196, the entire contents of which are incorporated herein by reference.

TECHNICAL FIELD

The present invention relates generally to an apparatus for guiding a surgical needle. In particular, the present invention relates to an apparatus for guiding a surgical needle for use in determining the position of entry of a surgical needle in the torso of a human patient during surgery.

BACKGROUND ART

Typically the point and angle of entry of a surgical needle (such as a biopsy needle) in a patient is first calculated by scanning the patient via an imaging technique such as computed tomography (CT) or magnetic resonance imaging (MRI) with imaging surface markers placed on the patient (such as the torso). The point of needle entry is typically selected with reference the most appropriate imaged position marker and the angle of needle entry in relation to the plane of the scan calculated by the scanning machine computer. An operator's then has to estimate the calculated needle entry angle for example with assistance from a protractor at the end of the bed before inserting the surgical needle into the patient.

After the initial needle entry into the patient, trial and error is then usually required to reposition the surgical needle via reentry of the surgical needle and further scans to make contact with the target (such as a lesion, fluid collection or during radio or microwave tissue ablation). The disadvantage of this procedure is the protracted operation time with multiple needle entries which can lead to discomfort and increased radiation exposure to the patient with CT scanning.

Known apparatus for guiding a surgical needle include the SeeStar device disclosed in http://apriomed.com/products/seestar/. The disadvantage with these known devices is that they are still relatively imprecise in matching the exact angle of entry of the surgical needle in axial and cranio-caudal planes to that calculated by an imaging machine, in that the apparatus has to be configured with the predicted angle of entry before attaching to the body of a patient, which may result in a change in the actual angle of entry after attachment if the patients body surface is not flat. In this way, known devices still frequently require repeated needle entry and scans to achieve a successful biopsy.

More recently, robotic automated image guided stereotactic apparatus are known which are designed specifically for use in determining the position and angle of entry of a needle into a human patient (used primarily in brain surgery). However these apparatus are bulky, costly to maintain with expensive software upgrades and difficult to operate, requiring highly specialist surgical skills.

Consequently there is a need for a cost effective and less intrusive diagnostic apparatus whereby the angle of entry of a surgical needle can be configured on the apparatus after placement on the body of a patient.

OBJECT OF THE INVENTION

It is an object of the invention to provide an apparatus for guiding a surgical needle that addresses at least some of the problems of the prior art, such as those discussed above.

Alternatively, it is an object of the invention to at least provide the public with a useful choice.

DISCLOSURE OF THE INVENTION

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

In a first preferred embodiment of the invention there is provided an apparatus for guiding a surgical needle comprising:
  a base configured for placement of the guide device on a patient;
  an arm attached to the needle guide support at one end and attached to a first arc member at a distal end;
  a needle guide support configured for attachment of a surgical needle guide for the surgical needle;
  a second arc member attached to the base
wherein
  the first arc member is attached to and configured to move on the second arc member to facilitate movement of the needle guide support in a cranio-caudal plane;
  the arm is attached to and configured to move on the first arc member to facilitate movement of the needle guide support in an axial plane; and
  the apparatus also comprises an angle marking device attached to the arm to indicate a vertical reference point for measuring the angle of tilt of the arm from the vertical reference point relative to the base.

Preferably, the angle marking device comprises a pointer configured to move relative to an angle scale to indicate an angle of incline of the needle guide support relative to the base.

Preferably, the needle guide support is a sliding carriage configured to accommodate needle guides of different diameters and to facilitate rotation of the needle guide within the needle guide support to allow the needle guide to be released from the needle guide support after entry of the needle into the patient.

In this way, release of the needle guide from the needle guide support allows manipulation and fine positioning of the needle within the patient.

Preferably, the base comprises at least one indicia to facilitate positioning of the apparatus on the patient.

In a second preferred embodiment of the invention there is provided a method of positioning a surgical needle in a patient with the apparatus of the present invention, the method comprising the steps:
  a. applying at least one position marker on the skin of a patient;
  b. scanning the patient in a scan plane to obtain an image of the lesion within the patient and the at least one position marker;
  c. calculating the required axial needle entry angle and depth of needle entry;
  d. mark a needle entry point on the skin of the patient corresponding to the intersection of the scan plane and the in relation to at least one of the imaged position marker from step b;

e. positioning a base of the apparatus on the skin of a patient aligned with the scan plane from step b and centred on the marked needle entry point from step d;
f. attaching a needle guide to a needle guide support of the apparatus;
g. moving an arm of the apparatus attached to the needle guide support at one end and attached to a first arc member at a distal end to the required axial needle entry angle calculated from step c using an angle marking device attached to the arm; and
h. inserting a needle into the patient via the needle guide to contact the lesion imaged in step b.

Preferably, the positioning of the base aligned with the scan plane in step e is facilitated by a laser line produced by a scanning apparatus (such as a computed tomography (CT) or magnetic resonance imaging (MRI) scanner) indicating the scanned plane.

Preferably, the method of positioning a surgical needle also optionally comprises the step after step g) and before step h) of moving the needle guide support via the first arc member attached to the base on a second arc member to a required angle in the cranio-caudal plane.

BRIEF DESCRIPTION OF THE FIGURES

The invention will now be described by way of example only and with reference to any one of the accompanying drawings in which.

SUMMARY OF THE INVENTION

Figure 1:
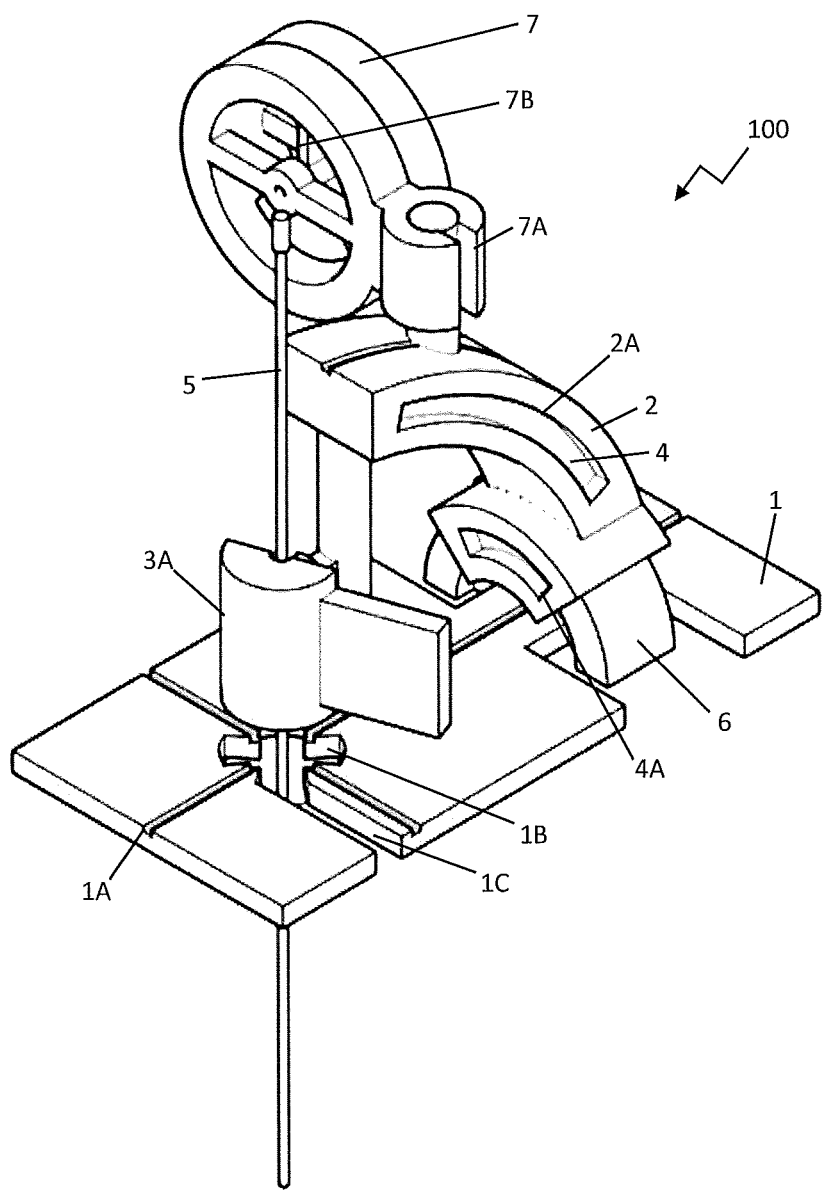
FIG. 1 shows a perspective schematic view of a preferred embodiment of the present invention in the form of an apparatus for guiding a surgical needle with a needle guide in a vertical position and an angle marking device in a side position.
Figure 2:
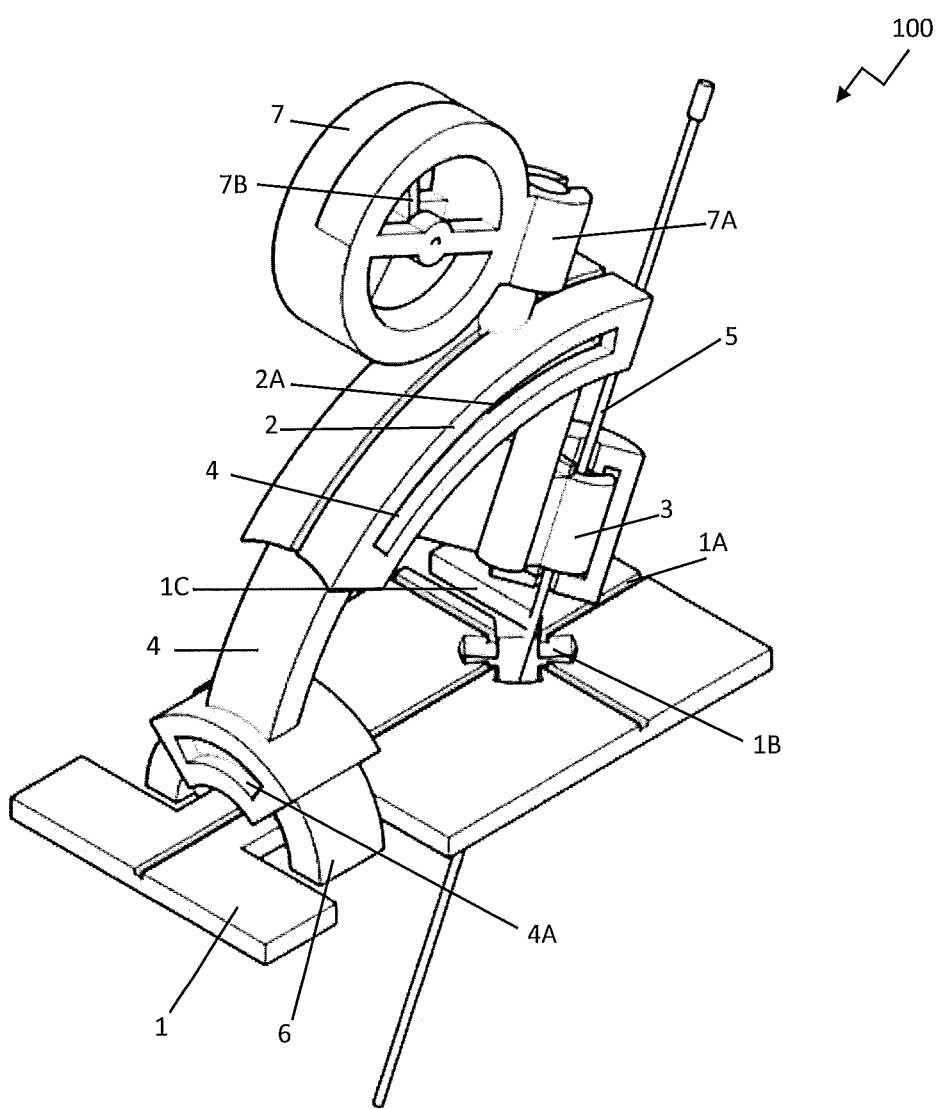
FIG. 2 shows a perspective schematic view of the preferred embodiment shown in FIG. 1 with the needle guide angled 25° in an axial plane.
Figure 3:
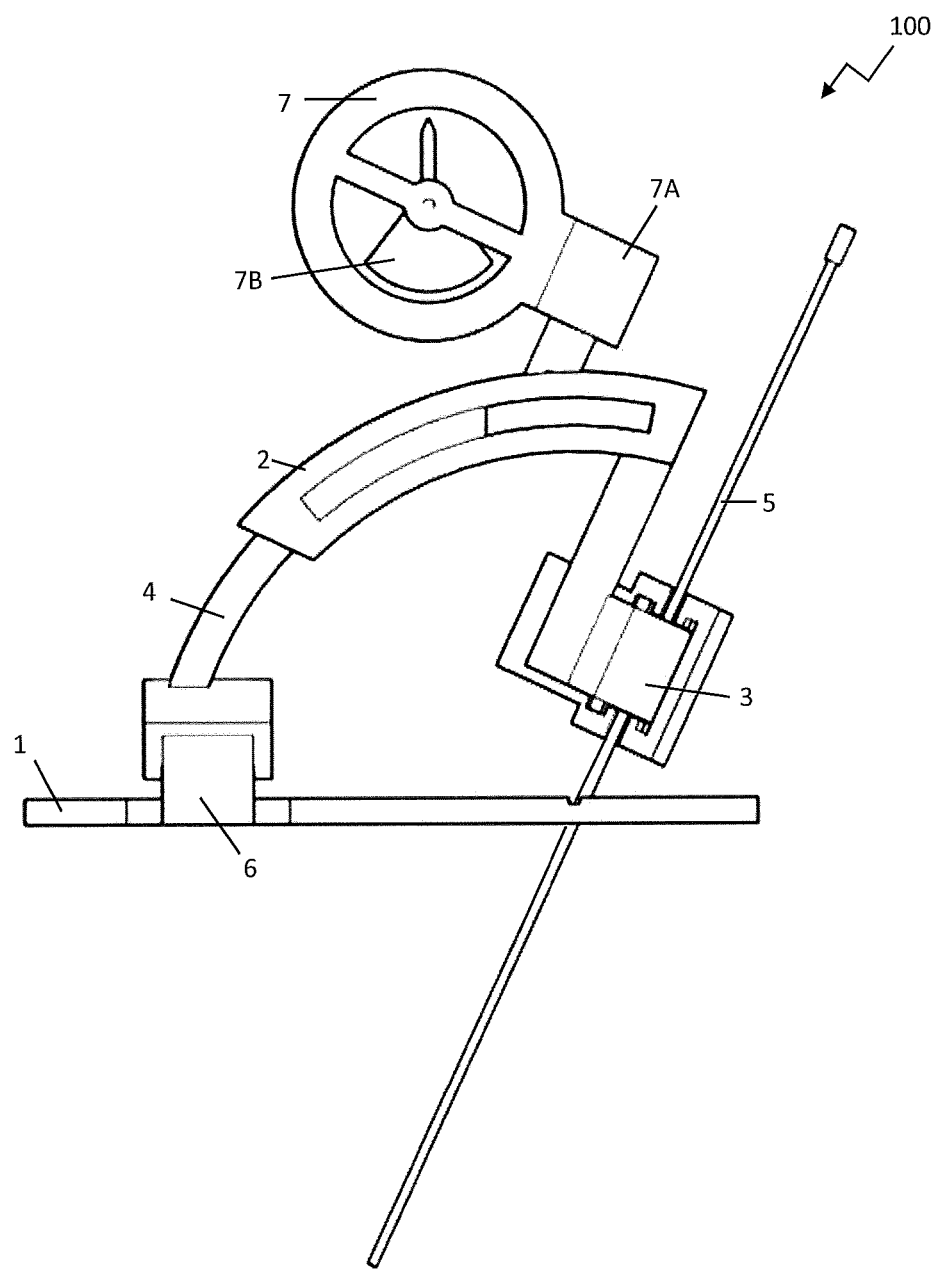
FIG. 3 shows a side view of the preferred embodiment shown in FIG. 2.
Figure 4:
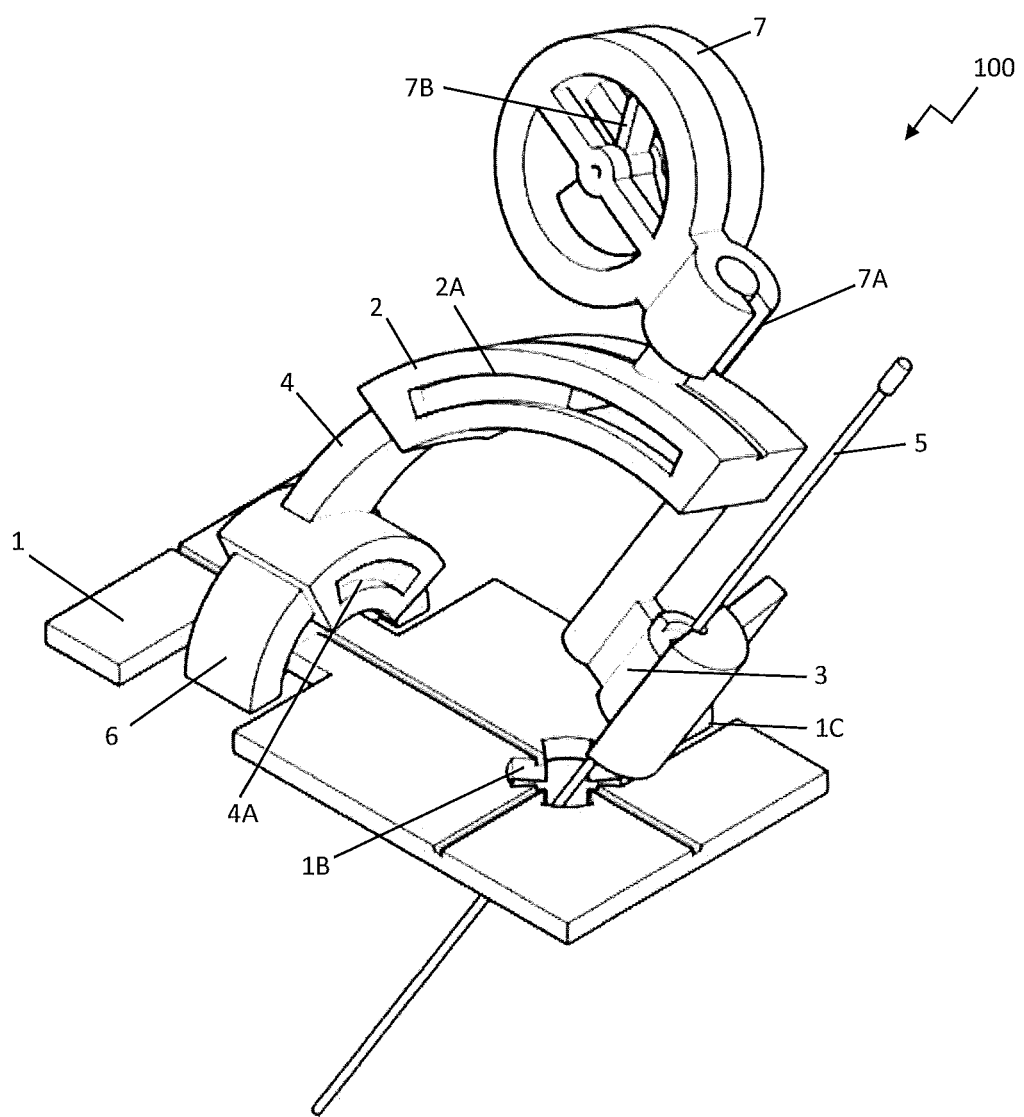
FIG. 4 shows a perspective view of the preferred embodiment shown in FIG. 1 with the needle guide angled 25° in the axial plane and angled 20° in a cranio-caudal plane.
Figure 5:
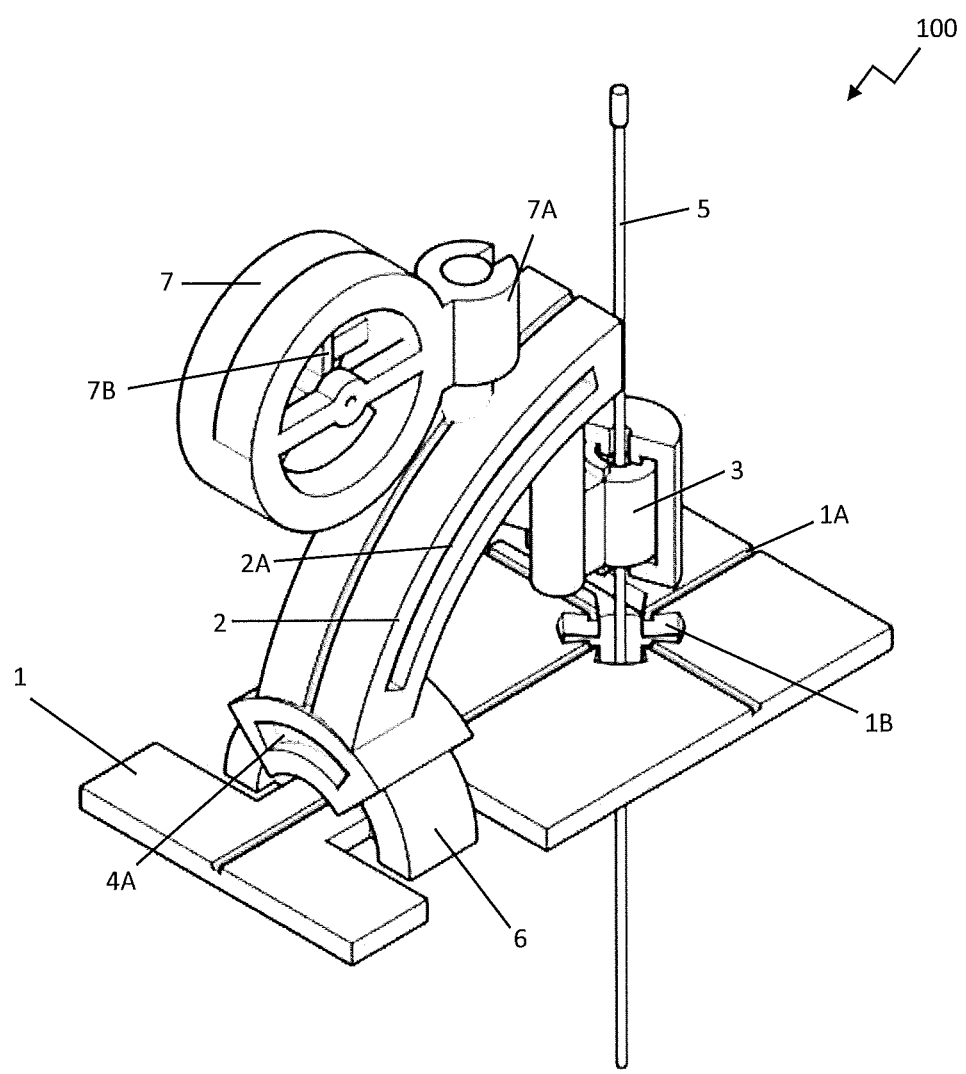
FIG. 5 shows a perspective view of the preferred embodiment shown in FIG. 1 with the angle marking device in a front position.
Figure 6:
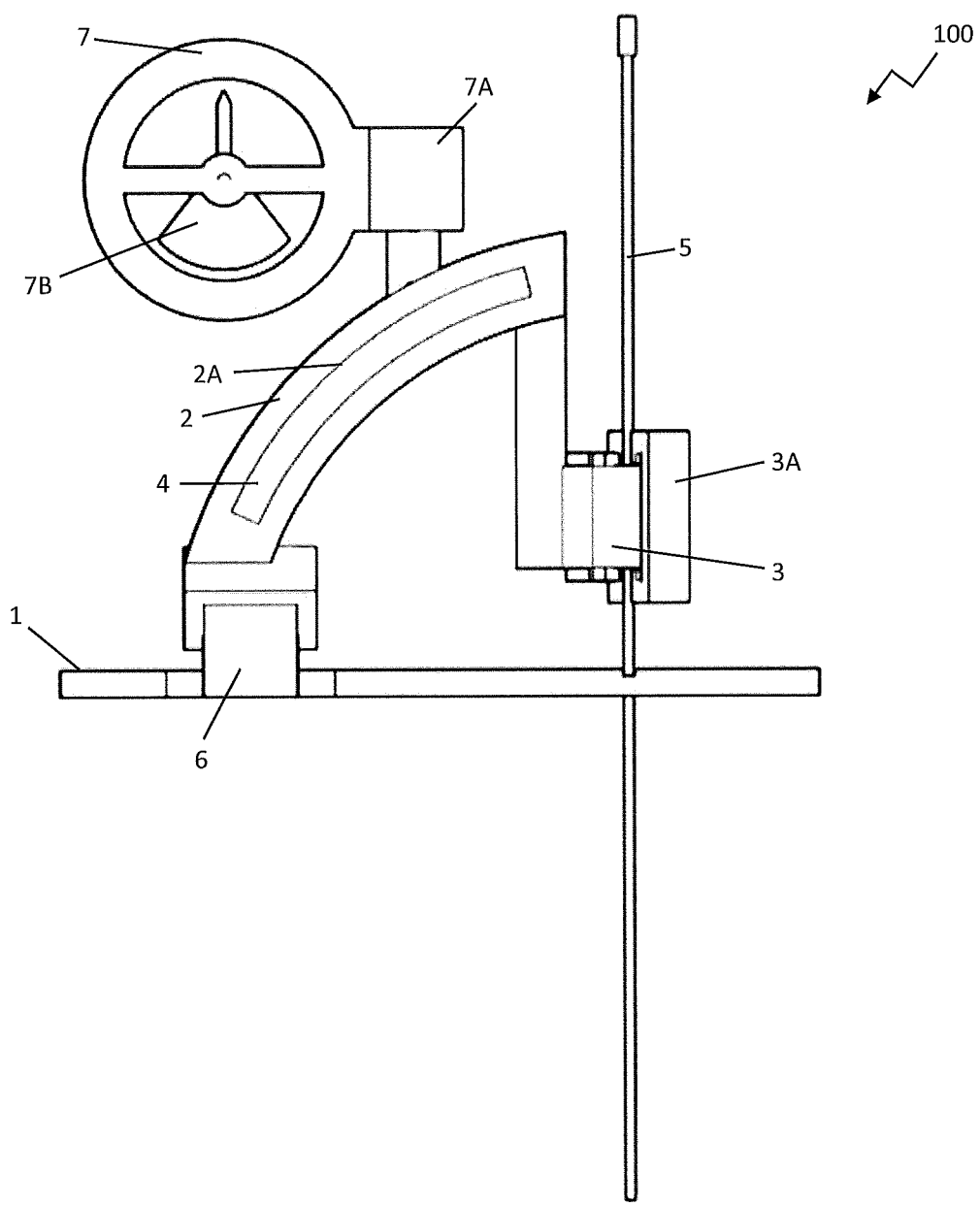
FIG. 6 shows a side view of the preferred embodiment shown in FIG. 5.
Figure 7:
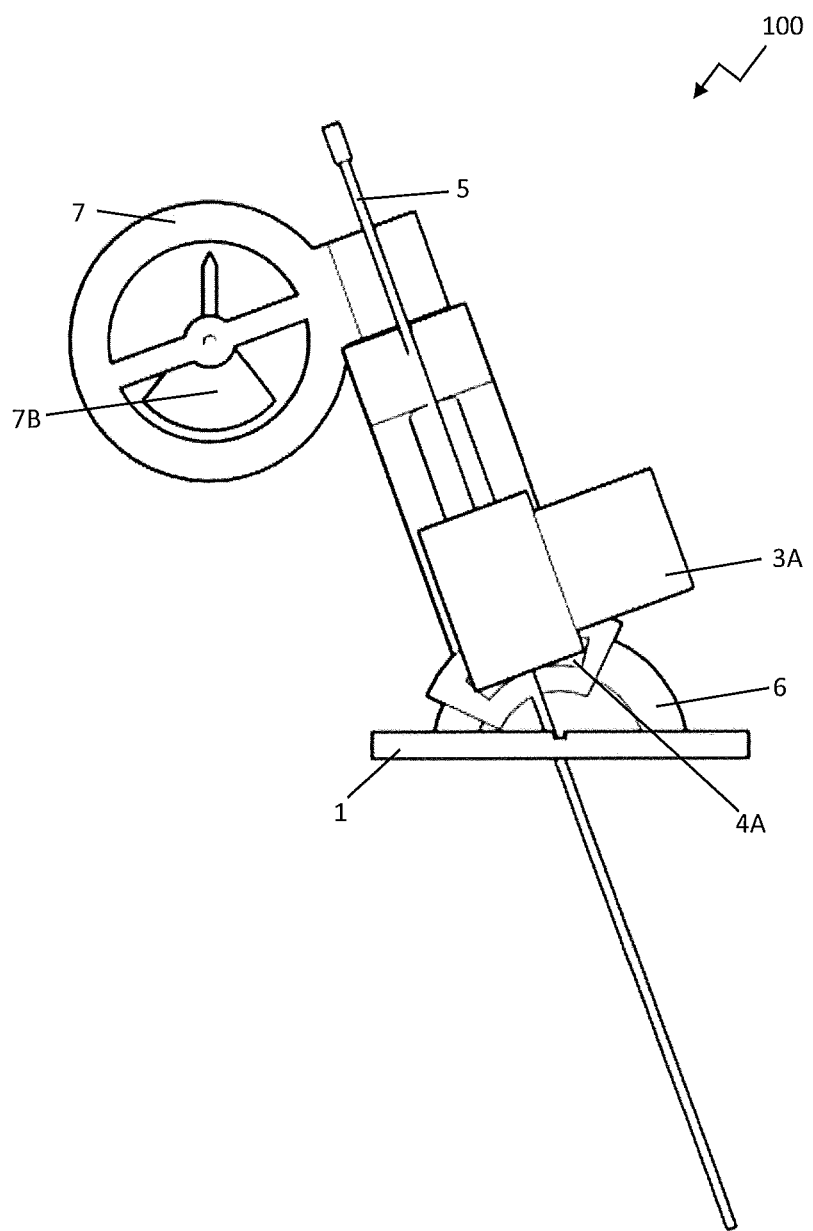
FIG. 7 shows a side view of the preferred embodiment shown in FIG. 1 with the needle guide angled 20° in a cranio-caudal plane.

The apparatus of the present invention provides for improved accuracy of entry of a surgical needle into a patient in an axial plane, and simultaneously in a cranio-caudal plane. The apparatus is held on a patient's skin aligned with a laser line marker at the correct horizontal position from a previous imaging scan of the patient to image the lesion inside the patient. Based on a scanned image of the patient and lesion and a computer determined calculation of the angle of entry and depth of a surgical needle required to contact the lesion within the patient, the apparatus can be used to position a surgical needle with the correct angular and radial coordinates to perform a biopsy of the target lesion. The depth of the needle is determined by graduated reference marks on the needle itself.

DETAILED DESCRIPTION OF THE INVENTION AND BEST MODES

Referring to FIGS. 1 to 9, in a preferred form of the present invention, an apparatus for guiding a surgical needle is generally indicated by arrow 100. The apparatus (100) comprises a base (1) configured for placement of the apparatus (100) on a patients skin. While the apparatus (100) is envisaged for use on a torso of a patient this should not be seen to limited the scope of the invention as the apparatus (100) could be used on other areas of a patents body to perform biopsy of a lesion.

The apparatus (100) also comprises an arm (2) attached at one end to a needle guide support in the form of a C-shaped clamp (3) and attached at its distal end to a first arc member (4). The C-shaped clamp (3) facilitates attachment of a surgical needle guide (5) for a surgical needle (not shown). The C-shaped clamp (3) has a sliding carriage (3A) configured to accommodate needle guides of different diameters and to facilitate rotation of the needle guide (5) within the C-shaped clamp (3) to allow the needle guide (5) to be released from the C-shaped clamp (3) after entry of the needle into the patient. In this way, release of the needle guide (5) from the needle C-shaped clamp (3) allows manipulation and fine positioning of the needle within the patient and utilisation of the full-length of the needle as it is not held up by the needle guide support (3/3A).

Figure 8:
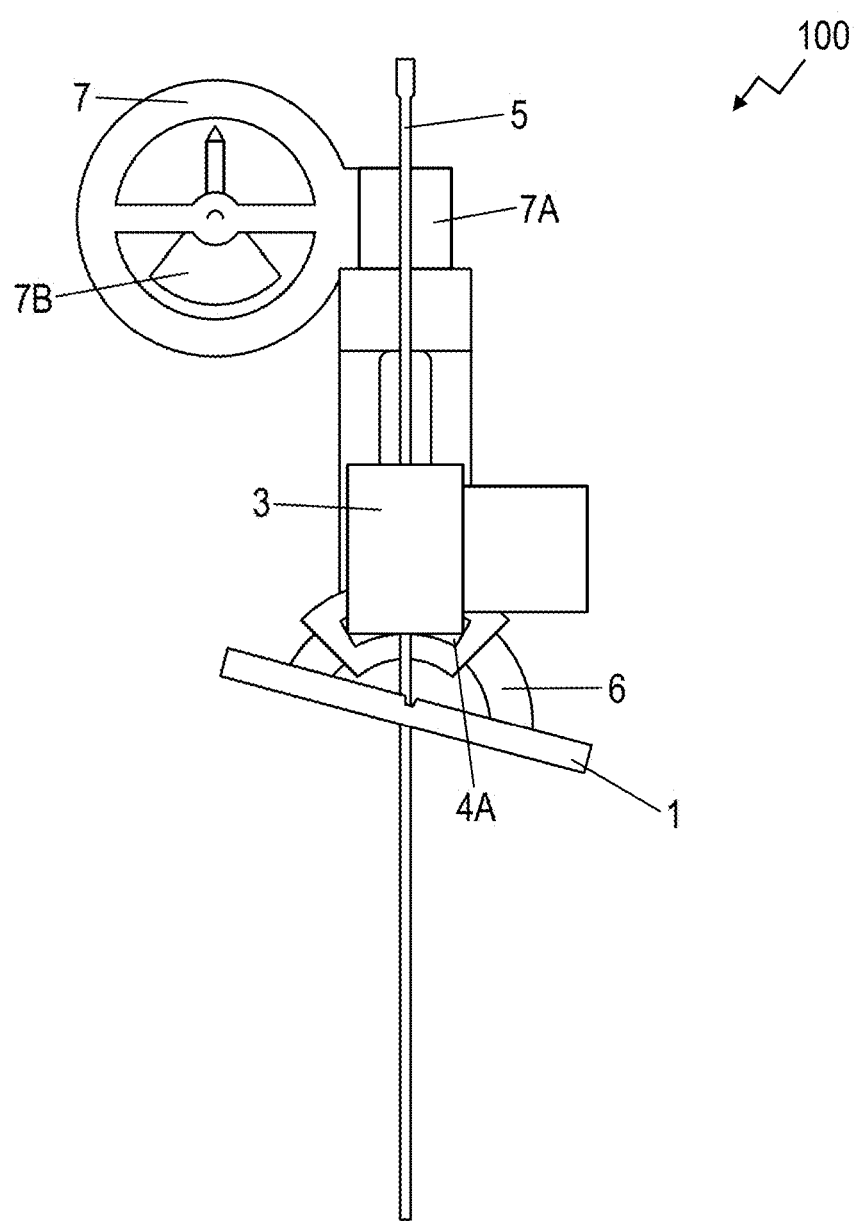
FIG. 8 shows a side view of preferred embodiment shown in FIG. 1 with a base angled 15°.
Figure 9:
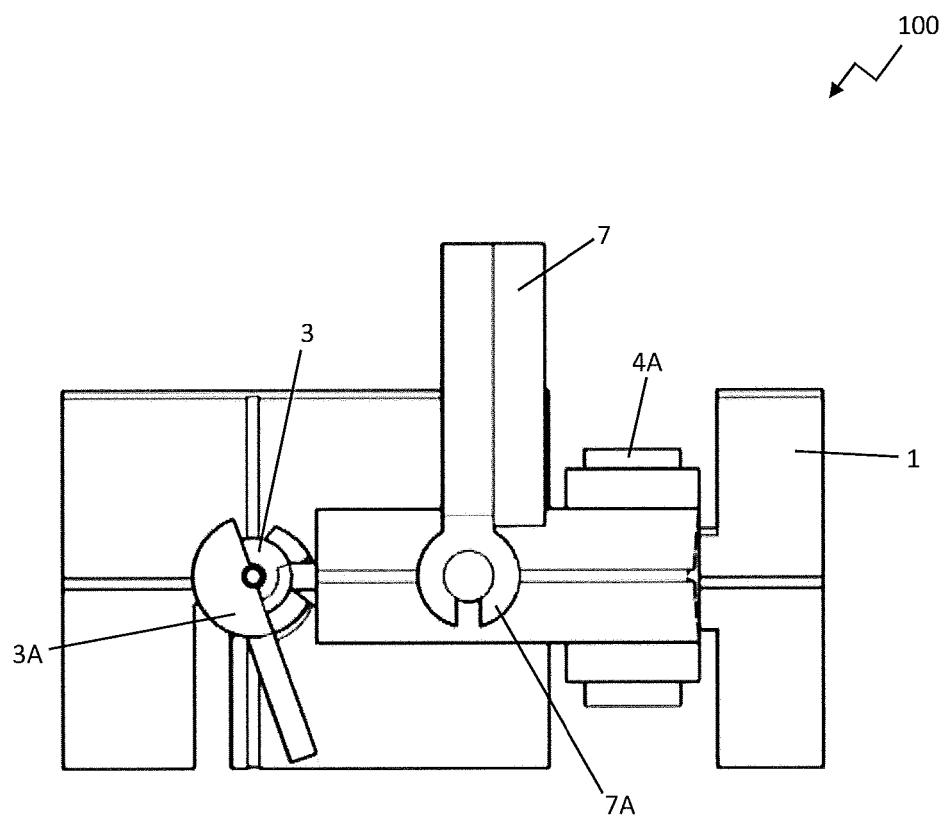
FIG. 9 shows a top view of the preferred embodiment shown in FIG. 1 with angle angle marking device in a front position.

The base (1) comprises at least one indicia in the form of a line groove (1A) to facilitate positioning of the apparatus (100) on the patient in relation to a laser line produced by a scanning apparatus (such as a computed tomography (CT) or magnetic resonance imaging (MRI) scanner) indicating the scanned plane. The needle guide (5) passes through the base (1) at aperture (1b) and its release from the apparatus (100) after insertion of the needle into the patient is facilitated by channel (1c). Referring to FIG. 8, the base (1) can be positioned on an angle surface of the patient's body while maintaining the vertical plane of the needle guide (5).

The arm (2) is curved and attached to the correspondingly curved first arc member (4) by accepting the first arc member (4) in a slot (2A) within the body of the arm (2). This should not be seen to limit the scope of the present invention however, as other forms of engagement of the arm (2) with the first arc member (4) could be used such as a tongue and groove arrangement. Extension of the arm (2) on the first arc member (4) facilitates movement of the needle guide support (3) in an axial plane.

The first arc member (4) is attached at one end to a second arc member (6) in the form of a semi-circle which in turn is attached to the base (1). The first arc member (4) is configured to move on the second arc member (6) to facilitate movement of the needle guide support in a cranio-caudal plane. The first arc member (4) moves on the second arc member (6) via acceptance of the second arc member (6) within a slot (4A) within the body of the first arc member (4).

The first arc member (4) and second arc member (6) can easily be locked into place with a fixing means such as at least one screw (not shown) to prevent the arcs (4, 6) moving while inserting the needle.

The apparatus (100) also comprises an angle marking device (7) attached to the arm (2) at a C-shaped clamp (7a) to indicate a vertical reference point for measuring the angle of incline or tilt of the arm (2) from the vertical reference point relative to the base (1). The angle marking device optionally comprises an angle scale (not shown) and a weighted pointer (7b). The C-shaped clamp (7a) facilitates rotation of the angle marking device (7) to a front (shown for example in FIG. 2) or side position (shown for example in FIG. 1) or any position in between to enable easy reading of the angle marking device (7) during use.

Alternatively, the angle marking device (7) could be a digital readout gyroscope without departing from the scope of the present invention.

The position of the base (1) does not necessarily need to be in a horizontal plane. It can be placed in any angle and as long as the angle marking device (7) matches the desired angle of entry, the surgical needle guide (5) and the surgical needle will be at that desired angle. In this way, the apparatus (100) has the advantage in that the desired angle of entry can be configured after the apparatus (100) has to be attached to the torso of the patient, thereby improving the accuracy of surgical needle entry in use and providing improved ease of use to the operator as no complicated calculation is needed to position the needle on the patients body which reduces the number of needle reentries and confirmatory scans needed which reduces the radiation exposure to the patient.

Figure 10:
FIG. 10 shows a surgical dummy with positional surface markers applied to its surface as part of the method of use of the preferred embodiment shown in FIG. 1.
Figure 11:
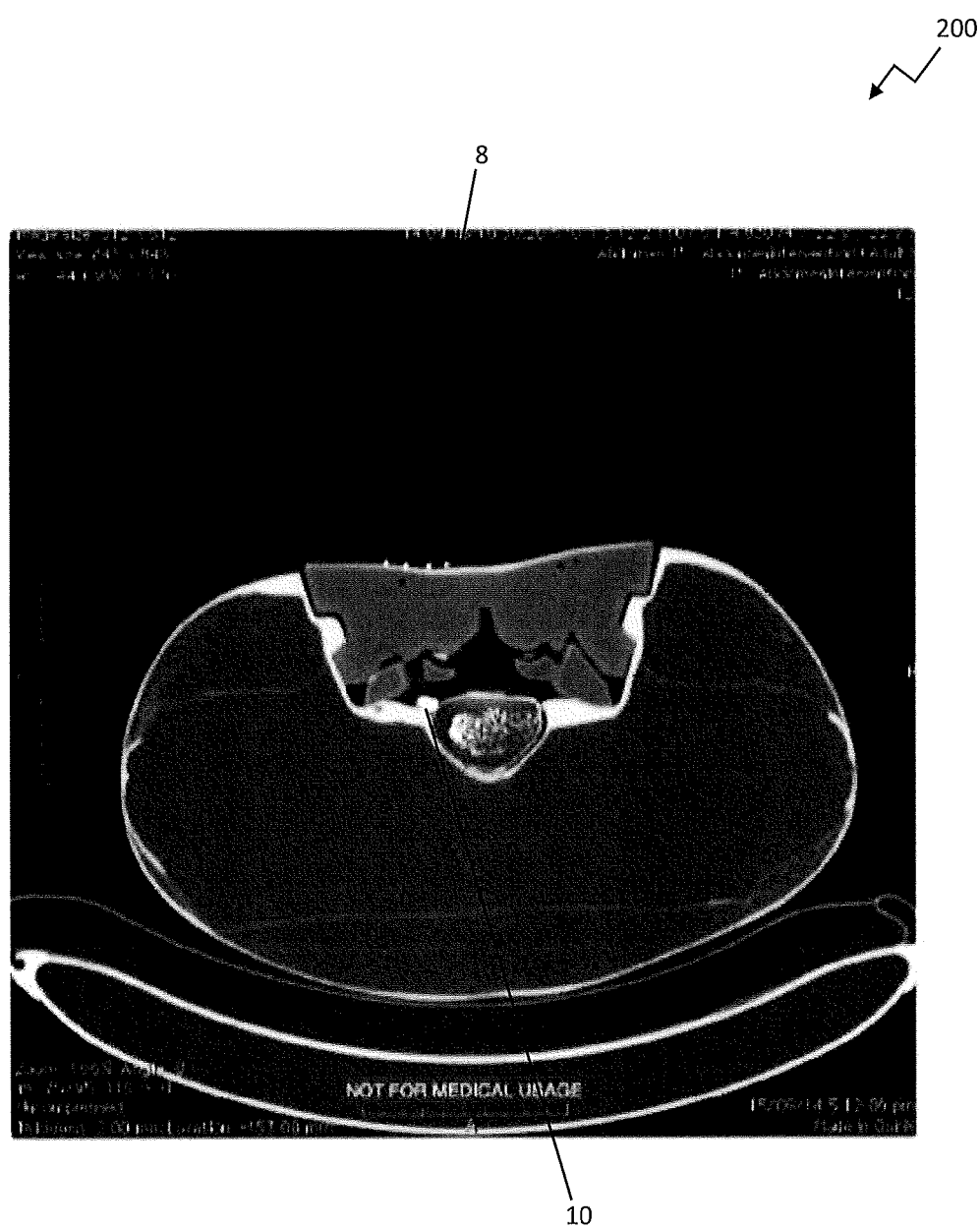
FIG. 11 shows a CT-scan of the surgical dummy shown in FIG. 10 with a target lesion for biopsy.
Figure 12:
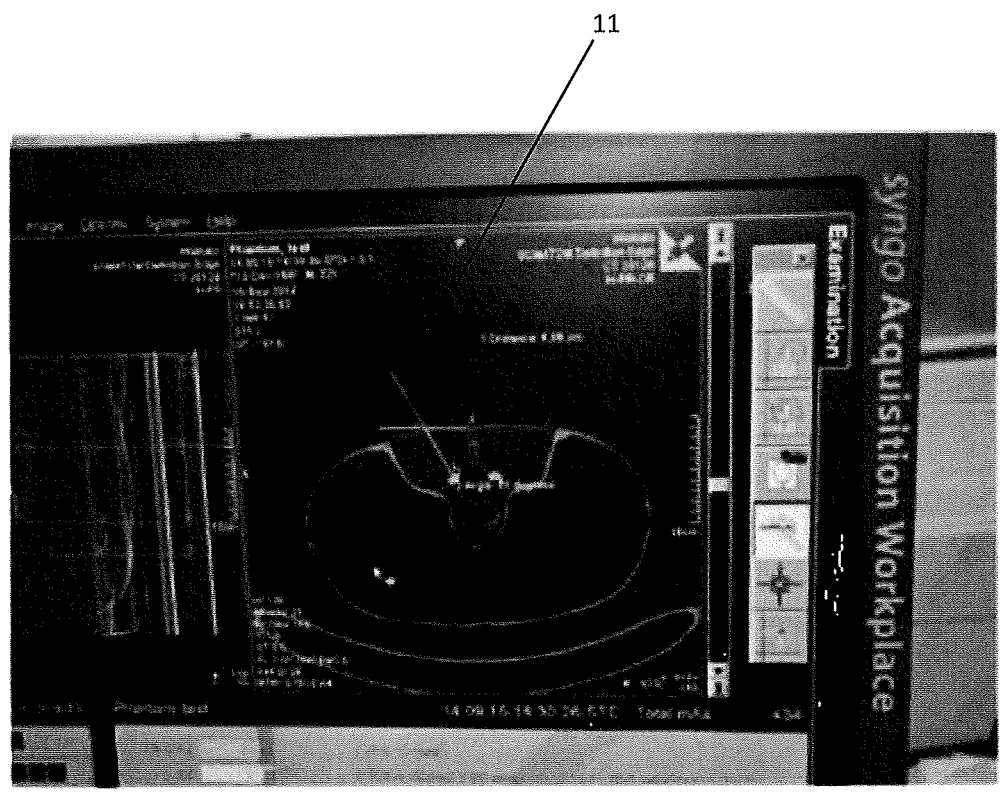
FIG. 12 shows a computer calculation of the angle of entry and depth of a surgical needle to perform biopsy of the lesion imaged in FIG. 11.
Figure 13:
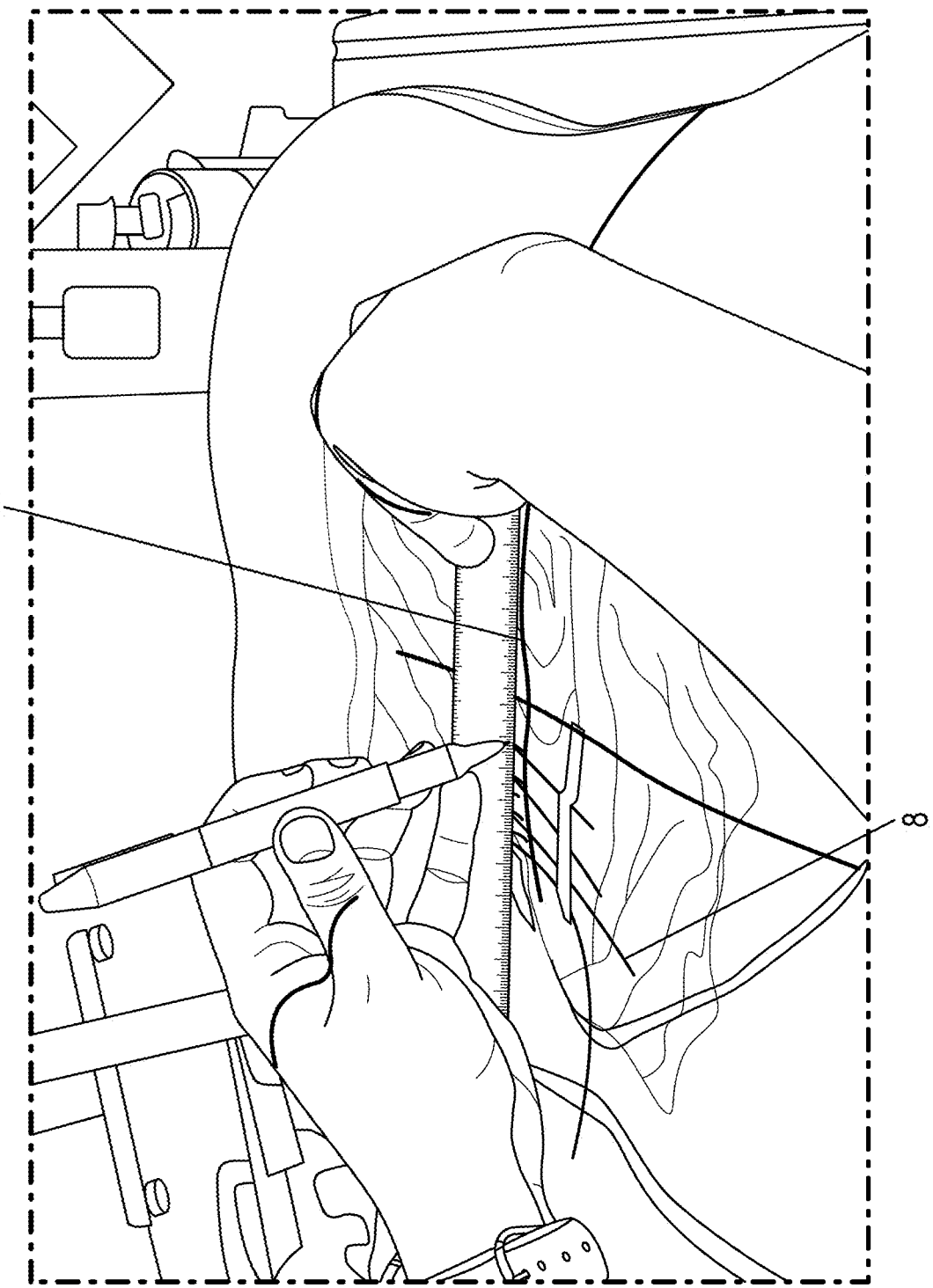
FIG. 13 shows marking of the expected surgical needle entry site in relation to the surface markers to the surgical dummy shown in FIG. 10.
Figure 14:
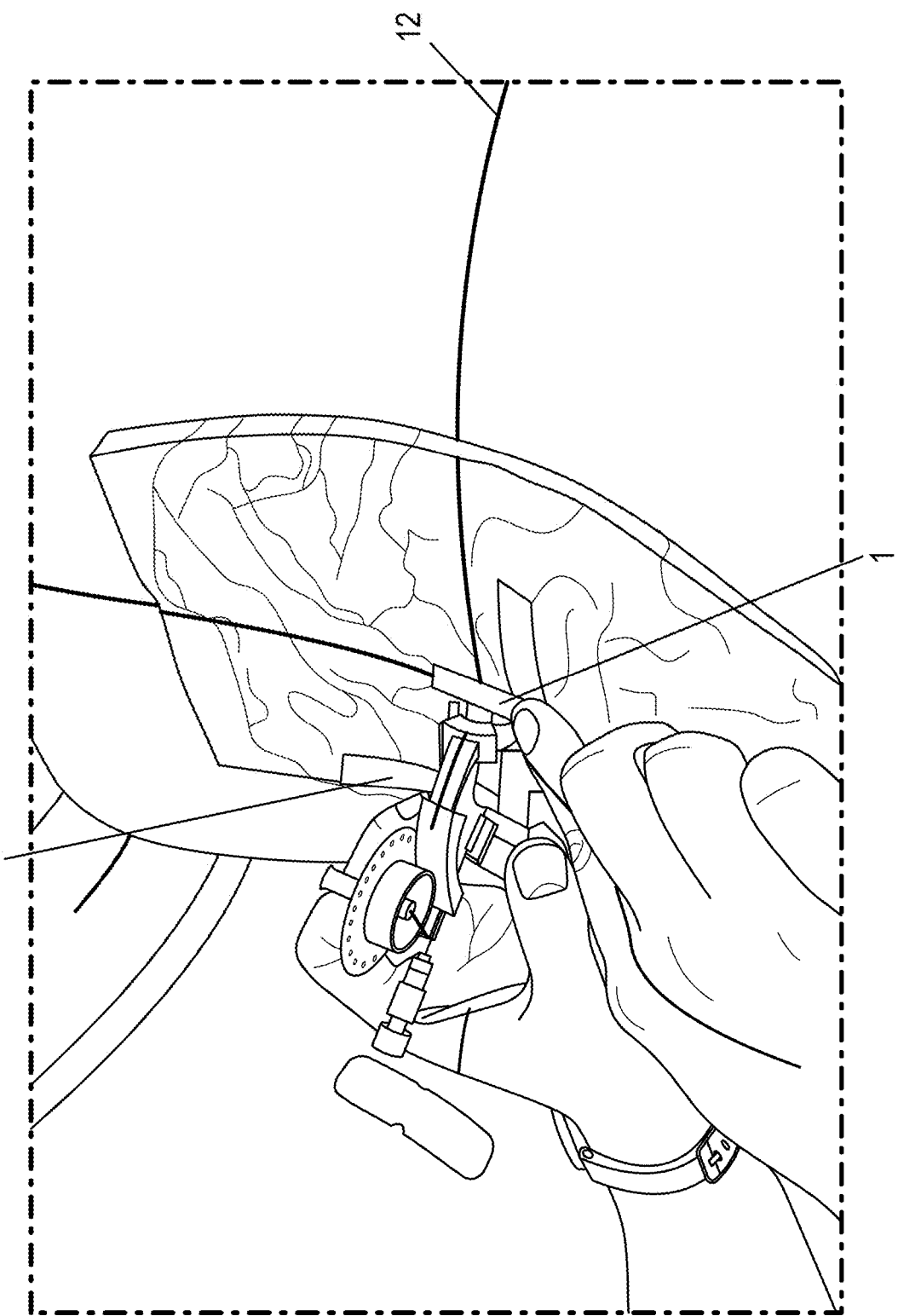
FIG. 14 shows alignment of the base of the apparatus of FIG. 1 with a laser line from the CT-scanning apparatus corresponding to the plane of the CT-scan image shown in FIG. 11.
Figure 15:
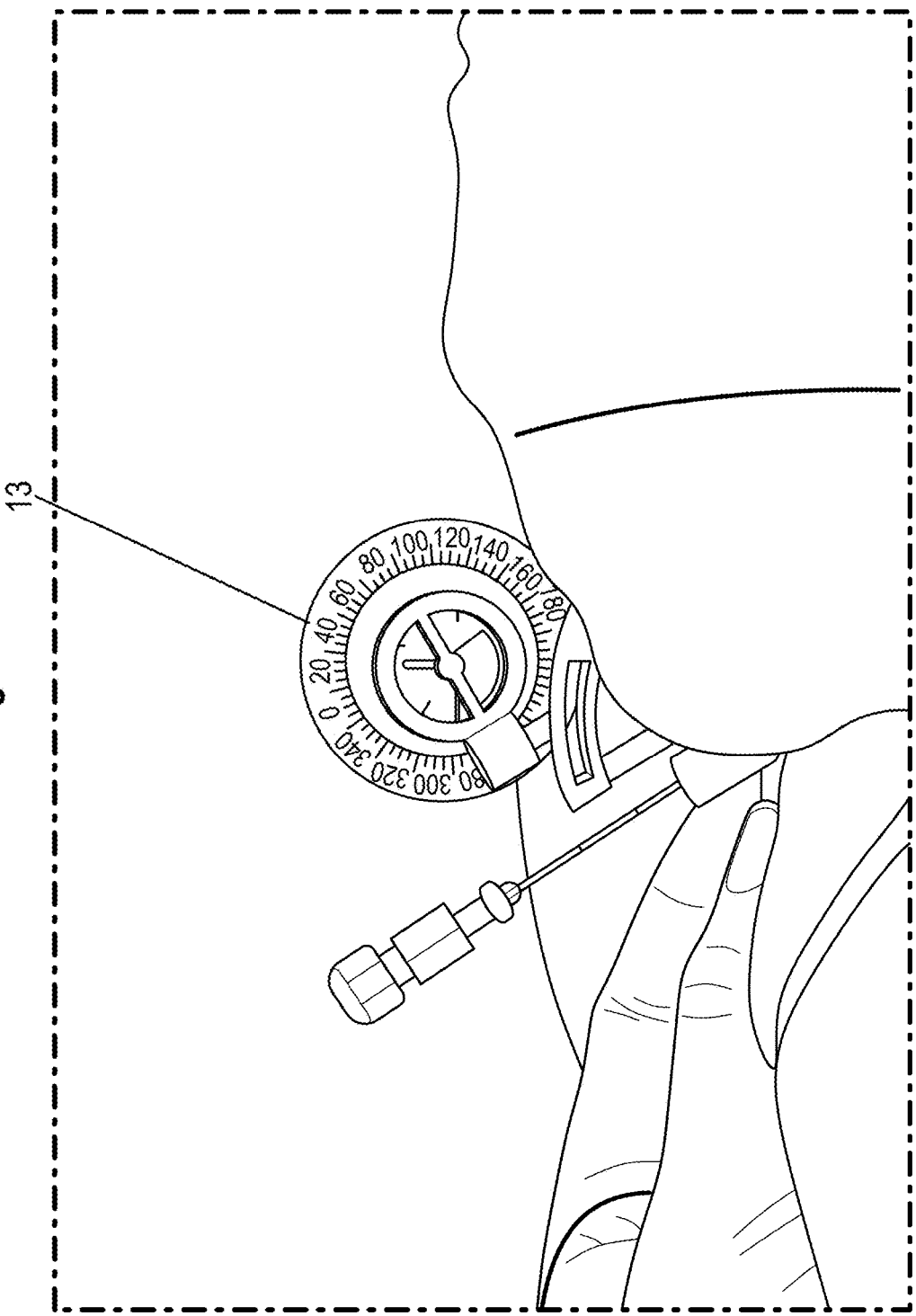
FIG. 15 shows angulation of the apparatus shown in FIG. 14 in an axial plane to correspond to the calculated angle of entry shown in FIG. 12.
Figure 16:
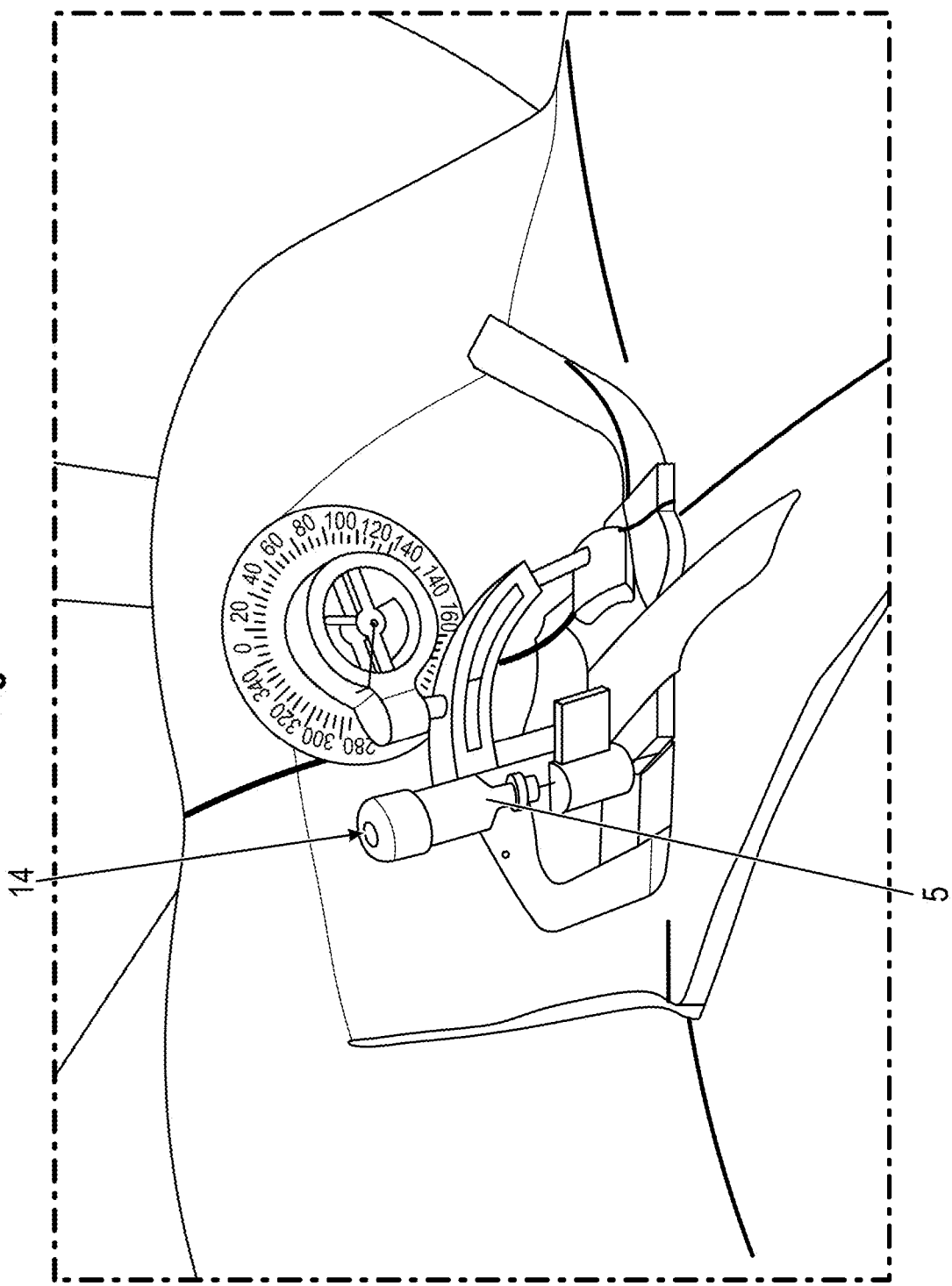
FIG. 16 shows the positioned apparatus shown in FIG. 15 with a surgical needle inserted into the surgical dummy.
Figure 17:
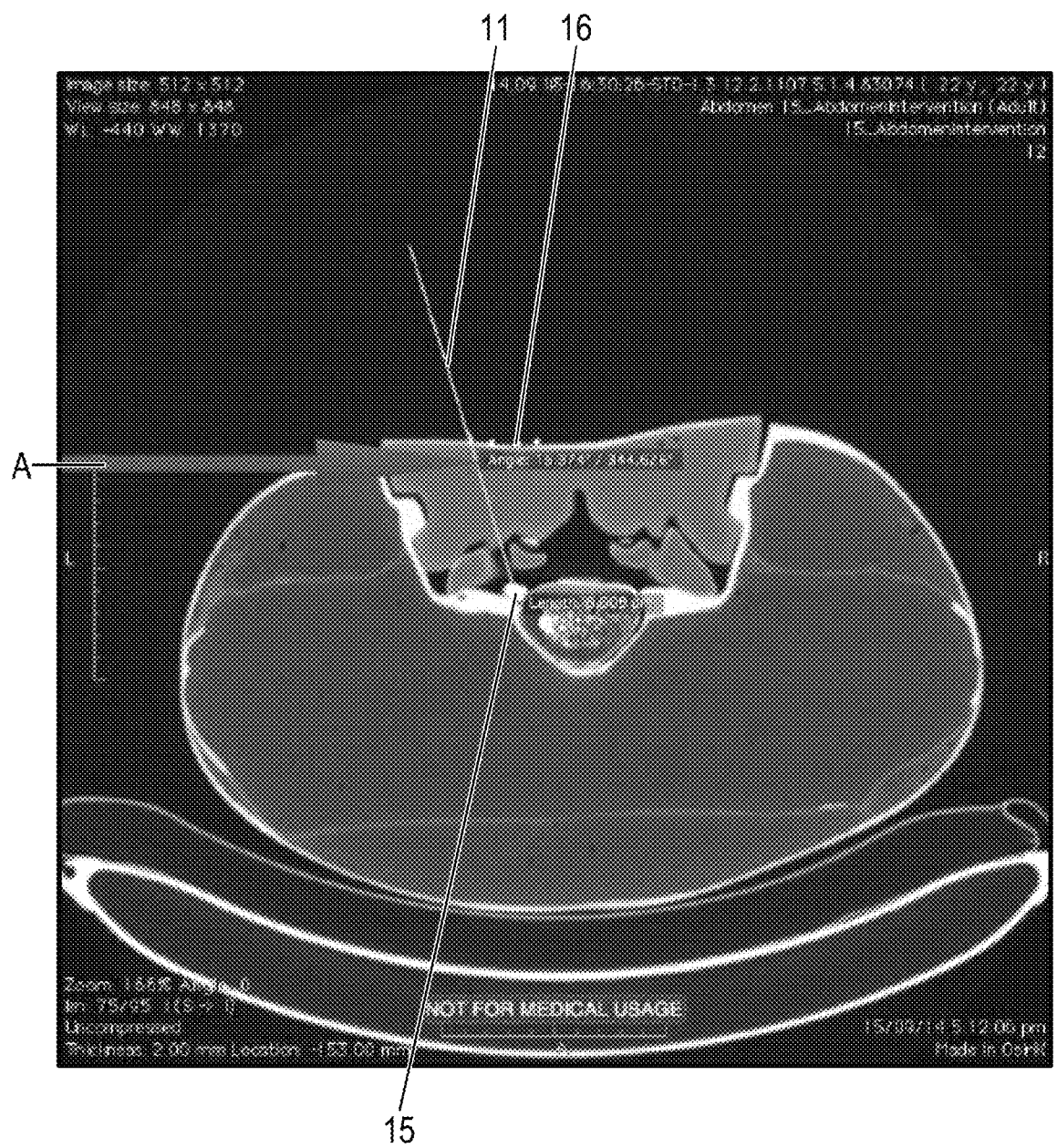
FIG. 17 shows a CT-scan in a first case study with a calculated angle and depth of entry to perform biopsy of a lesion.

Referring to FIGS. 10 to 23, in use a number of position markers (8) are applied on the skin of a patient (indicated by surgical dummy torso (9) (shown in FIG. 10). The patient is scanned with an imaging machine such as a computed tomography (CT) or magnetic resonance imaging (MRI) scanner. The resulting scan along a particular scan plane (200; shown in FIG. 11) is used to obtain an image of the lesion (10) within the patient and the position markers (8). A computer calculates the required axial needle entry angle and depth of needle entry (shown in FIG. 12 as 11). A needle entry point is marked on the skin of the patient corresponding to the intersection of a scan plane laser line (indicated as 12 on FIG. 13) and the nearest or most suitable path determining imaged position marker (8) (for example, if an internal organ is in the path indicated by the nearest imaged position marker). The base (1) of the apparatus (100) is fixed on the skin of a patient via tape and aligned with the laser scan plane line (12) and centered on the marked needle entry point (see FIG. 14). Before positioning the apparatus (100) on the skin of the patient, a needle guide (5) is attached to a C-shaped clamp (3). The arm (2) is moved on the first arc member (4) to the required axial needle entry angle as previously computer calculated using the angle marking device (shown in FIG. 15 as a protractor scale 13). A needle (shown as 14 on FIG. 16) is then inserted into the patient through the needle guide (5) at the correct needle entry angle to contact the lesion (10) via insertion of the needle to the required depth via graduated reference marks on the needle itself (not shown). If needed the needle guide support (5) can be also moved to a required angle in the cranio-caudal plane via moving the arm (2) via movement of the first arc member (4) on the second arc member (6).

Trial 1

Figure 18:
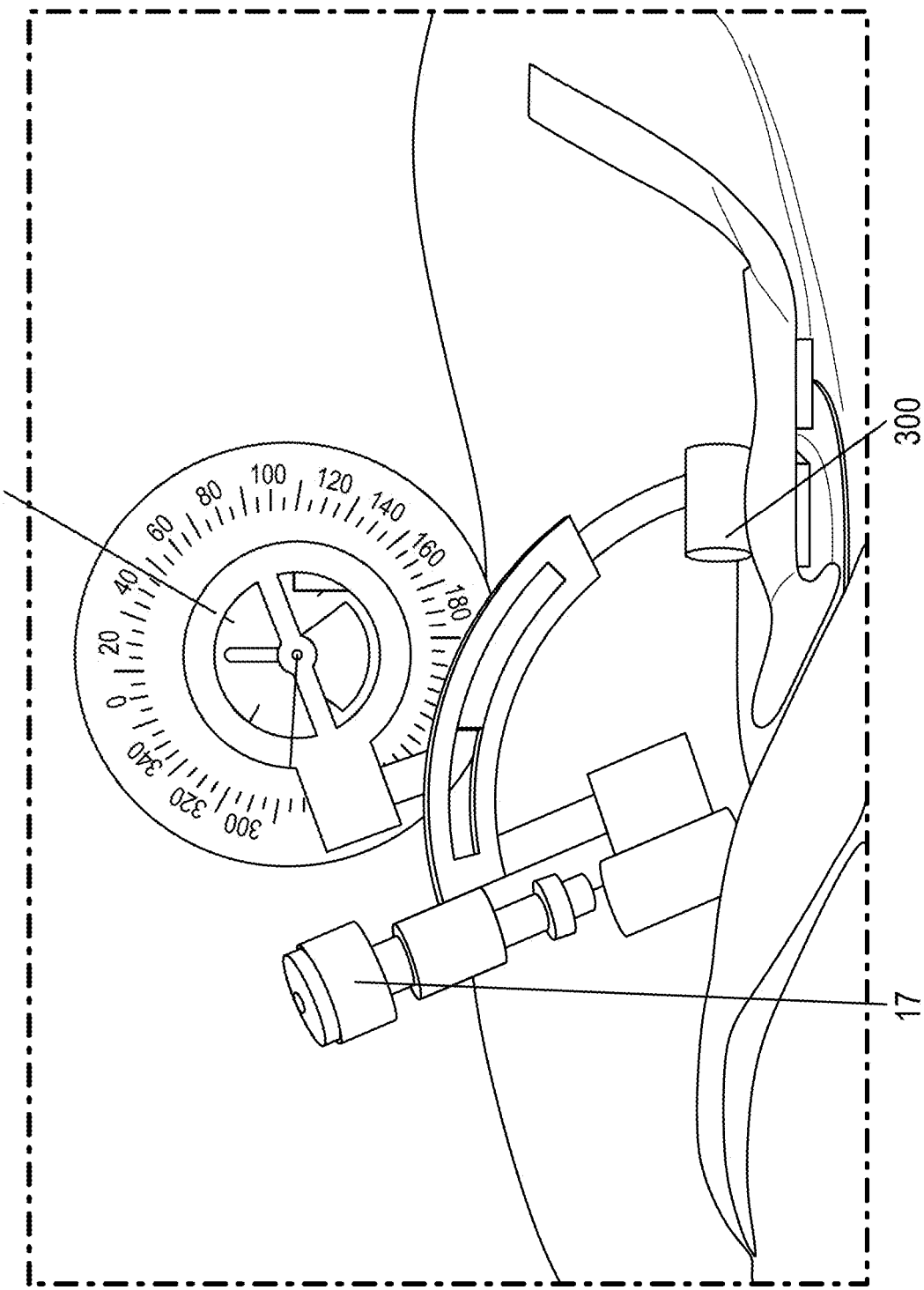
FIG. 18 shows the apparatus of FIG. 1 positioned on the torso of the surgical dummy shown in FIG. 17 with surgical needle inserted and angled at 15° in an axial plane corresponding to the calculated angle of entry shown in FIG. 17.
Figure 19:
FIG. 19 shows a CT-scan of the surgical dummy after insertion of the surgical needle shown in FIG. 18.
Figure 20:
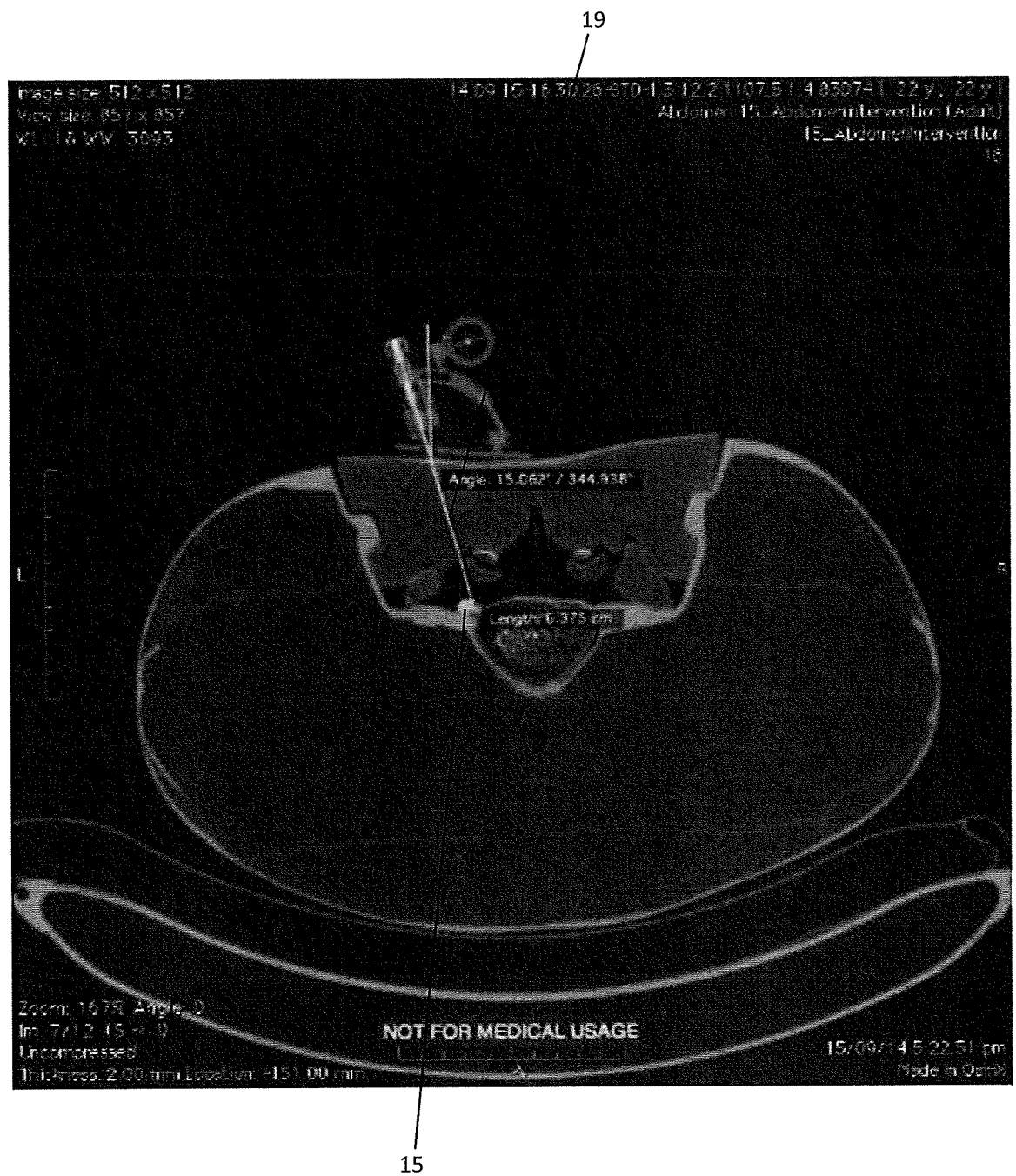
FIG. 20 shows the CT-scan shown in FIG. 19 with a computer calculated needle tract projected to hit the target lesion.

The results of a first trial case study are shown in FIGS. 17 to 20. A CT-scan of a lesion (15) and position markers (16) also shows a computer calculated required angle of entry of 15.374° and a required depth of entry of 6.609 cm to perform biopsy of the lesion (15) indicated at arrow A. FIG. 18 shows the apparatus (300) positioned on the patient with a surgical needle (17) inserted at the required 15° angle in an axial plane as indicated by pointer (18). FIG. 19 shows a CT-scan of the surgical dummy with initial insertion of the surgical needle (19) shown in FIG. 18 after a single needle entry at the required angle of entry (15°). FIG. 20 shows a CT-scan with the needle (19) fully inserted to the required depth of entry to hit the target lesion (15).

Trial 2

Figure 21:
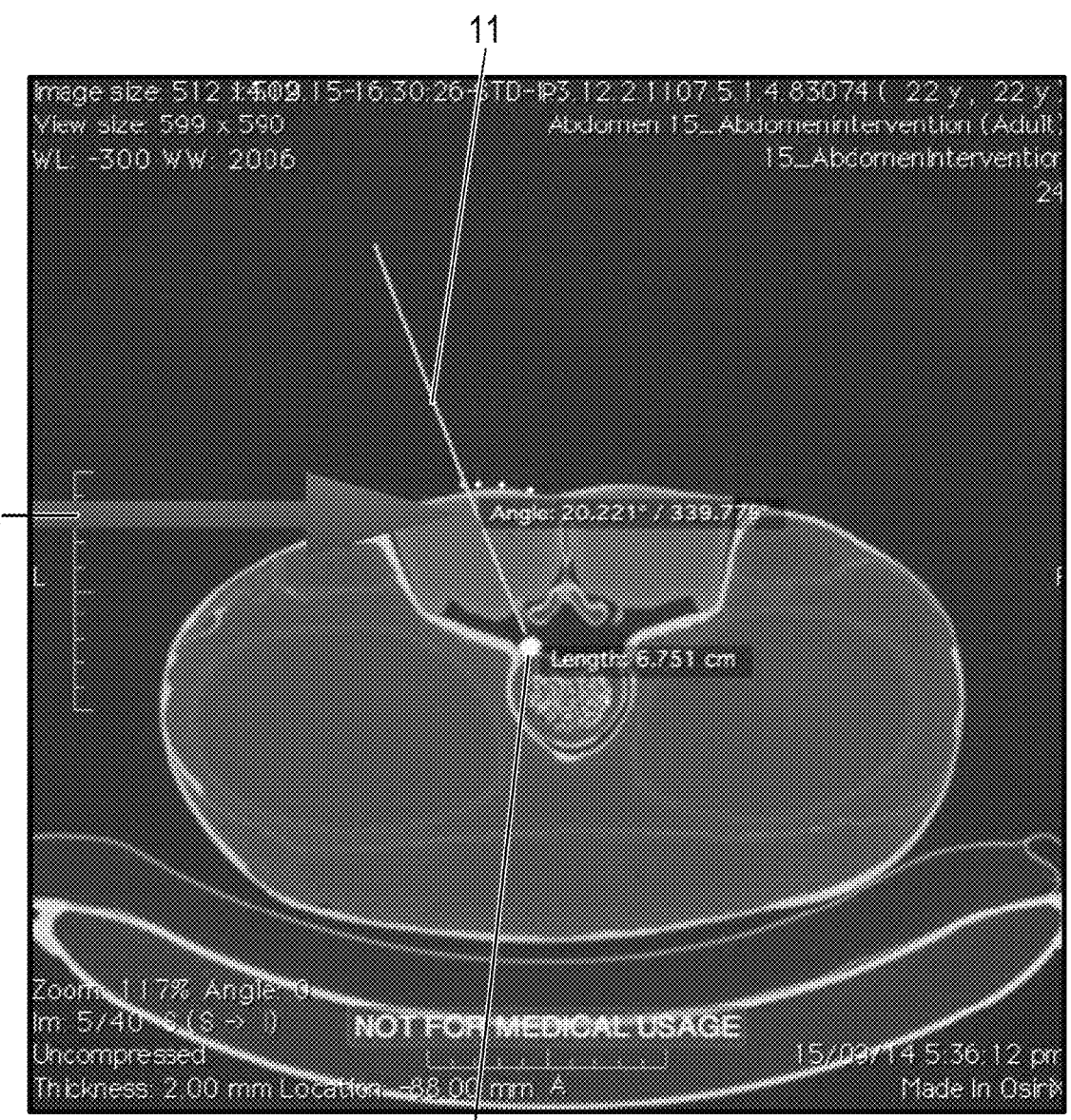
FIG. 21 shows a CT-scan in a second case study with a calculated angle and depth of entry to perform biopsy of a lesion.
Figure 22:
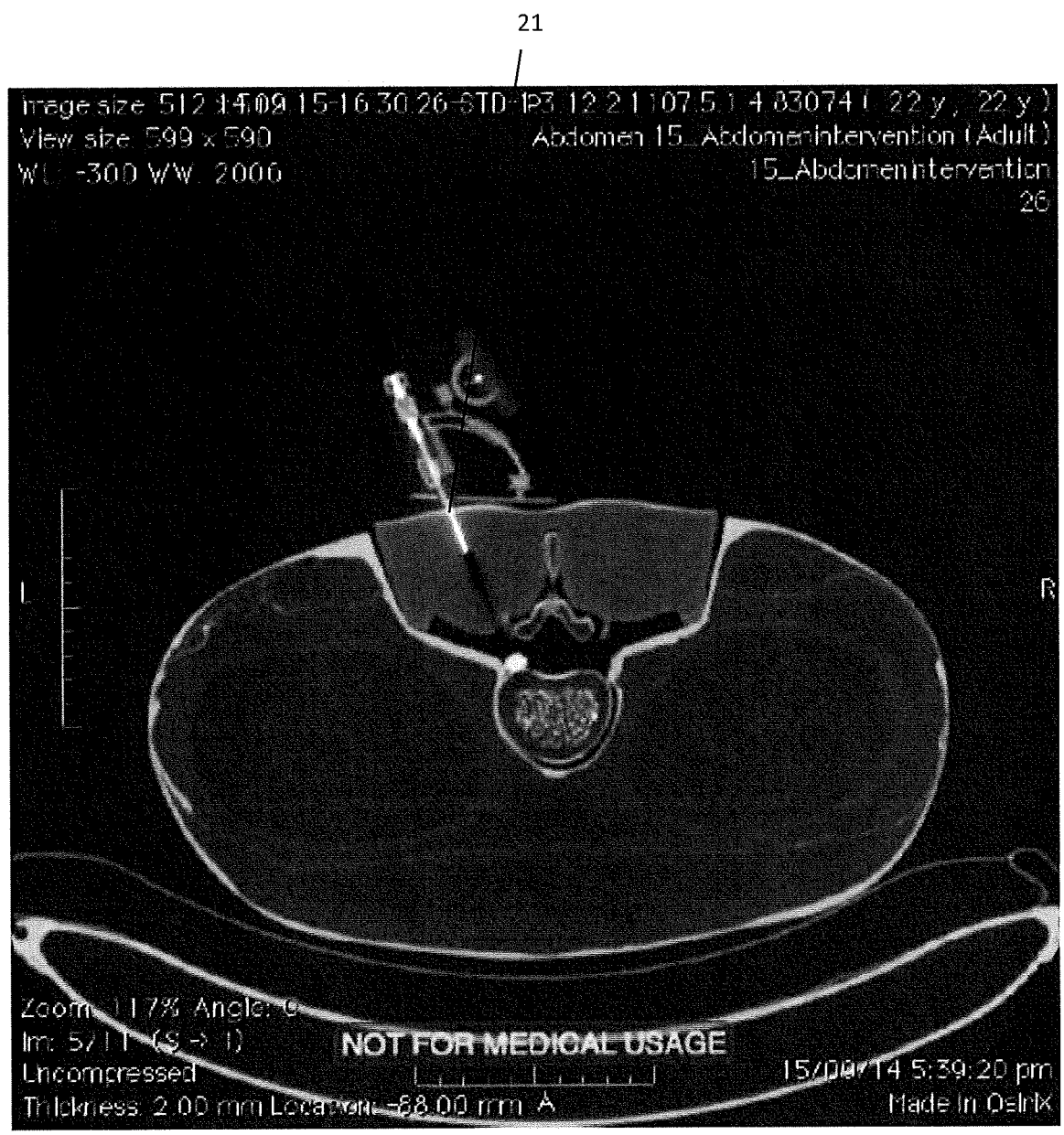
FIG. 22 shows a CT-scan of the surgical dummy after insertion of the surgical needle shown in FIG. 21.
Figure 23:
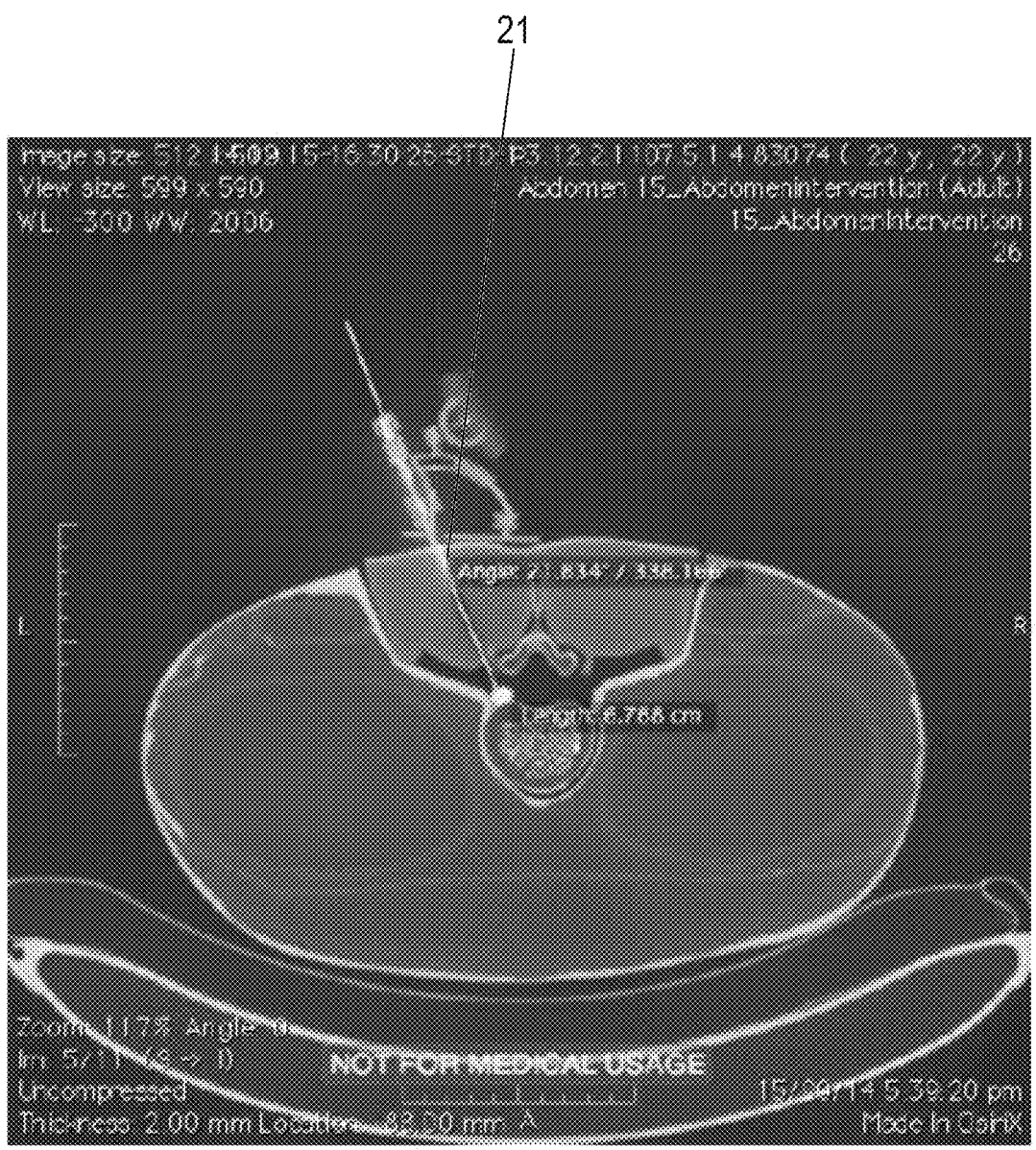
FIG. 23 shows the CT-scan shown in FIG. 22 with a computer calculated needle tract projected to hit the target lesion.

The results of a second case study are shown in FIGS. 21 to 23. FIG. 21 shows a CT-scan with a calculated needle entry indicated by arrow B with a calculated angle of entry of 20.221° and a depth of needle entry of 6.751 cm required to perform biopsy of a lesion (20). FIG. 22 shows a CT-scan of the surgical dummy with initial insertion of the surgical needle (21) after a single needle entry at the required angle of entry (20°). FIG. 23 shows a CT-scan with the needle (21) fully inserted to the required depth of entry to hit the target lesion (20).

ADVANTAGES

The present invention offers notable advantages over the prior art including:
    improved accuracy of angle of entry of a biopsy needle
        into a patient's torso at any angle of incline in an axial plane and in a cranio-caudal plane thereby providing a less invasive procedure to the patient by reducing the need for multiple needle entries;

improved ease of use over existing biopsy procedures; and improved procedural speed providing real-time or near real-time monitoring, thereby reducing radiation exposure dose.

ALTERNATIVES/MODIFICATIONS

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

Aspects of the present invention have been described by way of example only and it should be appreciated that modifications and additions may be made thereto without departing from the scope thereof as defined in the following claims.

What I claim is:

1. An apparatus for guiding a surgical needle comprising:
   a base configured for placement of the apparatus on a patient;
   a needle guide support configured for attachment of a surgical needle guide for the surgical needle;
   a curved arm attached to the needle guide support at one end and attached to a correspondingly curved first arc member at a distal end;
   a second arc member attached to the base;
   wherein
   the correspondingly curved first arc member is attached to and configured to move along the second arc member to facilitate movement of the needle guide support in a cranio-caudal plane;
   one of the curved arm and correspondingly curved first arc member has a slot and the other one of the curved arm and correspondingly curved first arc member is received in the slot, so that the curved arm is attached to and configured to move along the correspondingly curved first arc member to facilitate movement of the needle guide support in an axial plane; and
   an angle marking device attached to the curved arm to indicate a vertical reference point for measuring an angle of tilt of the curved arm from the vertical reference point relative to the base.

2. The apparatus as claimed in claim 1 wherein the angle marking device comprises a pointer configured to move relative to an angle scale to indicate an angle of incline of the needle guide support relative to the base.

3. The apparatus as claimed in claim 2 wherein the needle guide support is a sliding carriage configured to accommodate needle guides of different diameters and to facilitate rotation of the needle guide within the needle guide support to allow the needle guide to be released from the needle guide support after entry of the needle into the patient.

4. The apparatus as claimed in claim 1 wherein the base comprises at least one indicia to facilitate positioning of the apparatus on the patient.

5. A method of positioning a surgical needle relative to a patient with the apparatus as claimed in claim 1, the method comprising:
   a. applying at least one position marker on the skin of a patient;
   b. scanning the patient in a scan plane to obtain an image of a lesion within the patient and the at least one position marker;
   c. calculating a required axial needle entry angle and depth of needle entry;
   d. marking a needle entry point on the skin of the patient corresponding to the intersection of the scan plane and the at least one position marker imaged in step b;
   e. positioning the base of the apparatus on the skin of a patient aligned with the scan plane from step b and centered on the marked needle entry point from step d;
   f. attaching the needle guide to the needle guide support of the apparatus;
   g. moving the curved arm of the apparatus attached to the needle guide support at one end and attached to the correspondingly curved first arc member at the distal end along the correspondingly curved first arm member to the required axial needle entry angle calculated from step c using the angle marking device attached to the curved arm; and
   h. inserting the needle into the patient via the needle guide to contact the lesion imaged in step b.

6. The method as claimed in claim 5 wherein the positioning of the base aligned with the scan plane in step e is facilitated by a laser line produced by a scanning apparatus indicating the scanned plane.

7. The method as claimed in claim 5 wherein the method also comprises the step after step g) of moving the needle guide support via the first arc member attached to the base along the second arc member to a required angle in the cranio-caudal plane.

8. The method as claimed in claim 6 wherein the scanning apparatus is one of a computed tomography (CT) scanner and a magnetic resonance imaging (M I) scanner.

* * * * *